United States Patent [19]

Triner et al.

[11] Patent Number: 5,451,773
[45] Date of Patent: Sep. 19, 1995

[54] NON-CONTACT PERFORATION/PINHOLE DETECTION SYSTEM FOR OPAQUE VESSELS

[75] Inventors: James E. Triner, Gates Mills; Howard Fein, Richmond Heights; Don W. Cochran, Gates Mills, all of Ohio

[73] Assignee: Pressco Technology, Inc., Solon, Ohio

[21] Appl. No.: 299,806

[22] Filed: Sep. 1, 1994

Related U.S. Application Data

[63] Continuation of Ser. No. 71,544, Jun. 4, 1993, abandoned.

[51] Int. Cl.⁶ .............................................. G01N 9/04
[52] U.S. Cl. ................................... 250/223 B; 356/240
[58] Field of Search .......................... 250/223 B, 208.1; 209/588; 356/240

[56] References Cited

U.S. PATENT DOCUMENTS

| | | | |
|---|---|---|---|
| 3,991,882 | 11/1976 | Fahnestock et al. | 209/588 |
| 4,074,809 | 2/1978 | McMillin et al. | 209/588 |
| 4,105,122 | 8/1978 | Flood et al. | 209/588 |
| 4,455,225 | 6/1984 | Morimoto et al. | 209/588 |
| 4,459,023 | 7/1984 | Reich et al. | 250/223 B |
| 4,580,045 | 4/1986 | Kulig | 250/223 B |
| 4,882,498 | 11/1989 | Cochran | 250/571 |
| 4,900,916 | 2/1990 | Cormack | 250/223 B |
| 4,943,713 | 7/1990 | Yoshida | 250/223 B |
| 4,972,093 | 11/1990 | Cochran et al. | 250/572 |
| 5,008,533 | 4/1991 | Lee, Jr. | 209/588 |
| 5,049,750 | 9/1991 | Hoshino et al. | 250/223 B |
| 5,072,127 | 12/1991 | Cochran et al. | 250/572 |
| 5,095,204 | 3/1992 | Novini | 250/223 B |

Primary Examiner—David C. Nelms
Attorney, Agent, or Firm—Fay, Sharpe, Beall, Fagan, Minnich & McKee

[57] ABSTRACT

A system for detecting a side wall perforation in containers operates non-invasively and at line speeds. A stream of similar containers are communicated to an inspection area. An exterior of each container is illuminated while the container is in the inspection area. Light from an interior of the container is focused, via a lens, to a video camera. Any perforate flaw in the container walls results in a point source of light in the container interior. Since the perforations are relatively small, the point source is created due to diffractive properties of the slit perforation. These diffractive properties facilitate obtaining an image of the flaw from the camera disposed to the interior of the container when the camera is mounted orthogonally to the perforation or parallel to the wall being inspected. In an other embodiment, the relative positions of the light source and camera are interchanged. A method for container inspection is also provided in connection with the afore-noted structure.

32 Claims, 5 Drawing Sheets

NON-CONTACT PERFORATION/PINHOLE DETECTION SYSTEM FOR OPAQUE VESSELS

This application is a continuation of U.S. patent application Ser. No. 08/071,544, filed Jun. 4, 1993, now abandoned.

BACKGROUND OF THE INVENTION

This application pertains to the art of automated video inspection and more particularly to inspection of containers.

The invention is particularly applicable to real-time inspection of similar containers traveling on a conveyor system and will be described with particular reference thereto. However, it will be appreciated that the invention has broader applications such as in any system in which inspection of a concave specimen for perforate flaws is desired.

Automated video inspection has become an accepted aspect of manufacturing. In fact, such automated inspection is often considered mandatory in connection with containers, particularly in the food and beverage service industry.

In the past several years, significant advances have been made in the connection of automated container inspection. A first improvement was directed to engineered lighting for such inspections. Theretofore, automated inspection had been loaded towards sophisticated inspection algorithms. Advantages of engineered lighting allowed for less complex algorithms while concurrently facilitating increased inspection accuracy and specimen integrity. Aspects of such engineering lighting may be found in U.S. Pat. Nos. 4,882,498 and 4,972,093 both entitled PULSED-ARRAY VIDEO INSPECTION LIGHTING SYSTEM, and assigned to Pressco Technology, Inc., the assignee of the subject application.

While the first application for engineered lighting was in connection with inspection of container ends, the area was promptly broadened to include inspection of the interiors of containers. An example of this type of inspection may be found in connection with U.S. Pat. No. 5,072,127 entitled ENGINEERED VIDEO INSPECTING LIGHTING ARRAY, also assigned to Pressco Technology, Inc.

While the foregoing markedly improved the automated inspection of containers, room for improvement remained. More particularly, perforate or pinhole container defects, such as those provided in container side walls, were not readily detectable by the afore-noted technology.

Conventional systems are extremely limited in their ability to detect container side wall defects. In one system, a large "turntable" physically contacts containers, temporarily removing them from a line by a vacuum/-sealing attachment on an open end. A light sensor is then disposed within the sealed container. Any detected light by this sensor is concluded to signify the presence of a defect. The system therefore creates no "image" to be obtained that would allow for placement or classification of a defect.

The present invention contemplates a new and improved system which overcomes the above-referred problems, and others, and provides the container perforation detection system with improved ability to detect such defects in container side walls.

THE SUMMARY OF THE INVENTION

In accordance with the subjection invention, a light source provides illumination to a specified area. A sequence or series of similar containers are communicated to this inspection area. Light is provided to an exterior surface of each container as it is disposed in the inspection area. Concurrently, a camera lens is focused to an interior portion of the specimen, which interior portion is isolated from the lighting source. Any perforate detected in the container walls will allow light to pass to the container interior. Insofar as most perforations are extremely small, physics of light diffraction causes such a perforate defect to appear as a point source of light in the container interior. As such, the defect may be detected by a camera disposed in the focal path of the lens.

In accordance with another aspect of the present invention, the acquired image is a digitized, still photograph of the container interior. The still photograph is obtained by either strobing the light source or an electronic shutter disposed with the camera lens. This allows for inspection on a continuous stream of article in rapid motion relative to a stationary camera/lighting unit.

In accordance with another aspect of the present invention, illumination of the container exterior is accomplished by either coherent or non-coherent lighting. This includes laser sources, inert gas strobes or solid-state lighting, the latter of which may include light emitting diodes or laser diodes.

In accordance with yet another aspect of the present invention, relative position of the camera and light in the above-summarized structure are interchanged. In this fashion, illumination is accomplished to the interior of the container while the camera is focused on the exterior.

Yet another aspect of the present invention provides a method for non-invasive, high-speed video inspection of containers in connection with use of the afore-summarized structure.

An advantage of the present invention is the provision of an inspection system for automated detection of perforate flaws in container walls.

Another advantage of the present invention is the provision of a system for inspection of container wall defects in a system that operates at a high rate of speed.

Yet another advantage is the provision of a container wall defect inspection system which operates non-invasively on each of a stream of containers.

Yet another advantage of the present invention is the provision of a container wall defect analysis system which accomplishes an imaging of a defective container side wall.

Yet another advantage of the present invention is the provision of a container defect analysis system which does not contact containers inspected thereby.

Further advantages will become apparent to one of ordinary skill in the are upon reading and understanding of the subject specification.

BRIEF DESCRIPTION OF THE DRAWINGS

This invention may take physical form in certain parts, and arrangements of parts, the preferred and alternate embodiments of which will be described in detail in this specification and illustrated in the accompanying drawings which form a part hereof and wherein.

DETAILED DESCRIPTION OF THE PREFERRED AND ALTERNATE EMBODIMENTS

Figure 1:
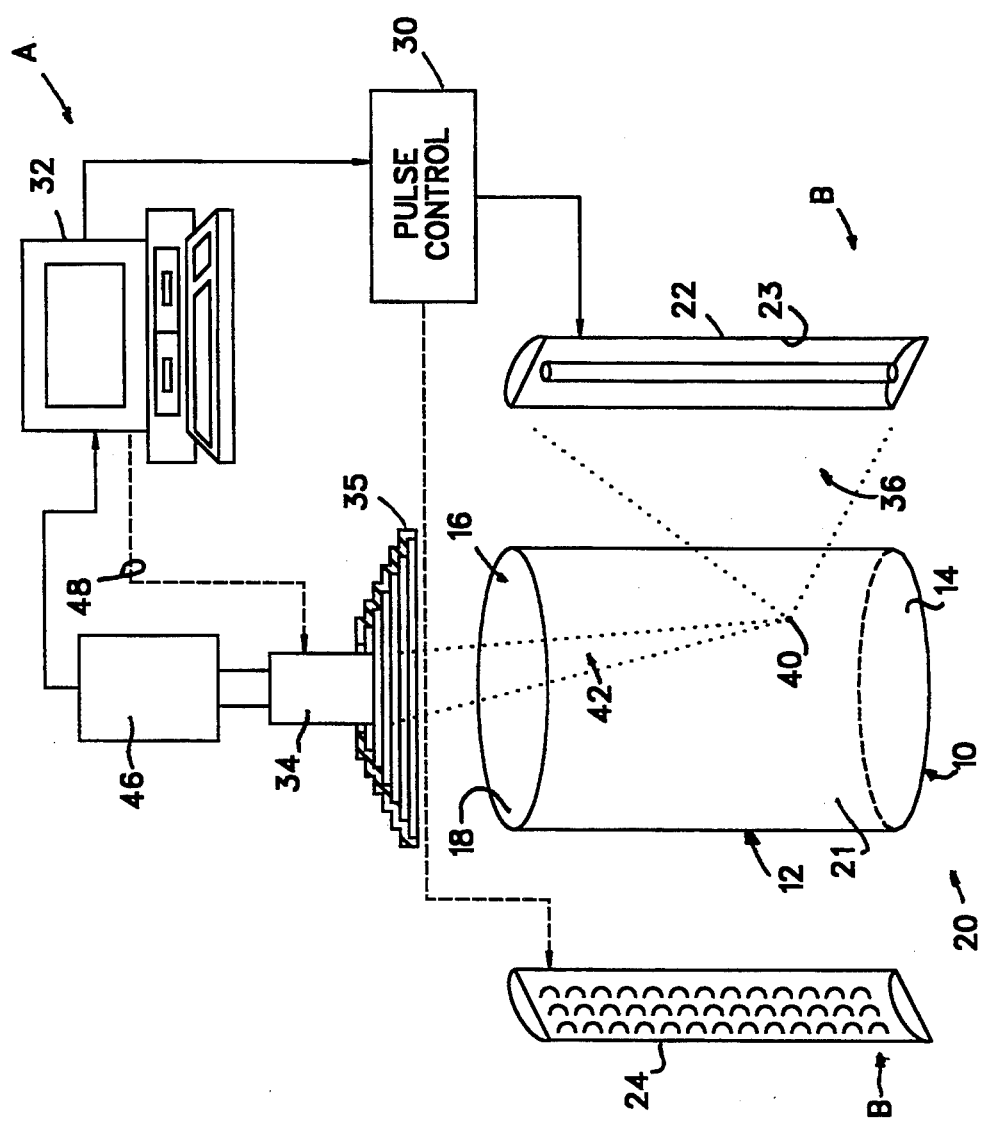
FIG. 1 illustrates an inspection system of the present invention employing an illumination subsystem of a first embodiment of the subject invention.

Referring now to the drawings wherein the showings are for the purposes of illustrating the preferred and alternate embodiments of the invention only, and not for the purposes of limiting the same, FIG. 1 illustrates an inspection system A employing exterior specimen lighting for perforate defect detection. Illustrated therein is a specimen 10 in the form of a generally cylindrical container having a continuous side wall 12, a bottom wall 14, an opening 16, and an interior wall 18. While a cylindrical specimen is illustrated, it will be appreciated that any substantially concave specimen may be suitably inspected with the disclosed structure.

In the illustration of FIG. 1, the specimen 10 is disposed within an inspection or lighting area illustrated generally at 20. In the embodiment of the figure, the inspection or lighting area 20 is defined relative to light emanating from a light source B such that exterior 21 of the side wall 12 is illuminated thereby.

Also in the illustration of FIG. 1, alternative structure for the light source B is illustrated. Included is a strobe lamp, such as an inert gas or xenon strobe 22. Such strobes advantageously provide high intensity illumination upon activation. Further, the strobes provide a very short duration illumination cycle which facilitates "freezing" of a specimen in motion relative thereto as will be described further below.

The illustrated, alternative light source B is formed from an array of solid-state lighting elements 24. The particulars associated with such array of solid-state lighting elements are described in connection with U.S. Pat. Nos. 4,882,498 and 4,972,093 both entitled PULSED-ARRAY VIDEO INSPECTION LIGHTING SYSTEM, the contents of which are incorporated herein by reference. Individual elements 26 of the array 24 are suitably comprised of solid-state light emitting diodes ("LEDs"), solid-state lasers having pulsed or modulated light, or the like. As noted by the incorporated patents, solid-state lighting advantageously facilitate long-life and minimal interstrobe and intrastrobe variations. It will be noted that a light source as used herein envisions any of the foregoing.

While light of any color may be utilized, a specified light spectrum/acquisition system may advantageously be selected to minimize any effect of light on image acquisition other than light of a specified wavelength constituent. Such is detailed in the contents of which are further incorporated by reference.

Either the inert gas strobe 22 or the solid-state lighting element array 24 are operatively connected to a pulse control circuit or a means 30. The pulse control means 30 allows for selective enablement of a light element connected thereto so as to allow timed activation thereof or control in lighting properties.

The pulse control circuit 30 is, in turn, placed under the direction of a computer means 32. The computer means 32 includes processing capability, memory storage (both volatile and non-volatile), as well as input-/output ("I/O") capabilities as will be appreciated by one of ordinary skill in the art.

A lens means 34 is secured such that its optical access is generally parallel to at least a portion of the side wall 12 of specimen or container 10. Further, the optical access of the lens 34 is directed generally to an interior portion 18 of the specimen 10 through opening 16. Relative orientations between the light source B and the lens means 34 facilitate isolation of a direct radiation path therebetween. An optic baffle 35 is also advantageously employed to minimize lighting artifacts as to the lens 34.

Figure 2:
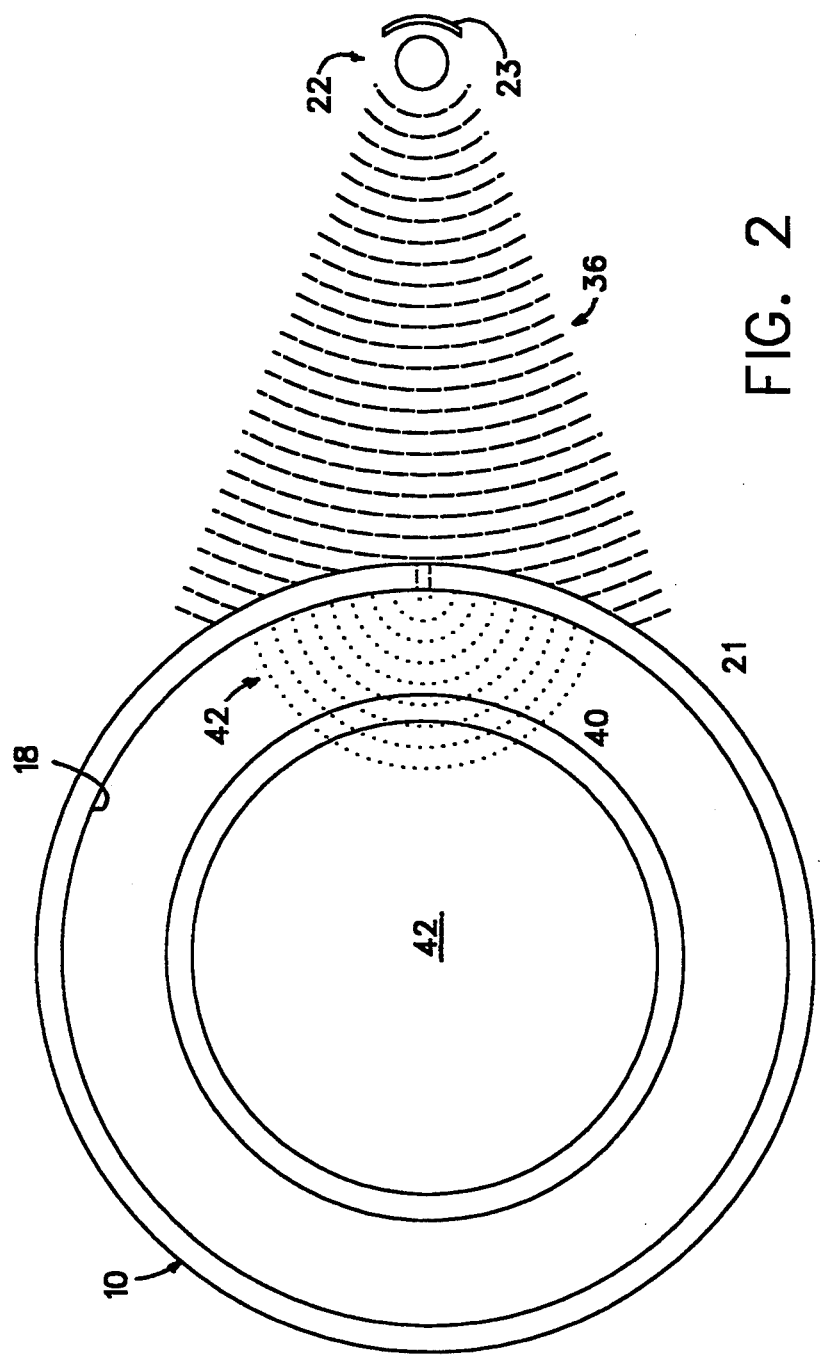
FIG. 2 illustrates the diffractive light property associated with an inspection of the subject system.

Illustrated in conjunction with the strobe 22 is illumination therefrom, a portion 36 of which is incident on a perforate defect or flaw 40 disposed within the side wall 12. Turning briefly to FIG. 2, illustrated is the incident light portion 36 emanating from the inert gas strobe 22 and an associated concave spherical or parabolic reflector 23, which together form the light source B. The incident light 36 impinges upon the exterior wall 21 of specimen 10. A portion of this light impinges upon the perforate defect or flaw 40. The relative size between the wave length of the incident light 36 and the defect 40 results in diffraction of light 36 which passes through the side wall 12 through the defect 40. It will be appreciated that diffraction results in the formation of a light point source at an exit of a slit system, such as is formed by the defect 40. Thus, a transmitted light portion 42 is passed to the interior of the specimen 10 as a point source defined from the interior wall 18 thereof. As the light becomes an effective point source, it is irradiated in all directions from the perforate defect or flaw such as that illustrated at 40.

With reference again to the illustration of FIG. 1, it will be noted that the relative orientation of the lens 34 to the interior of the specimen 10 allows for utilization of the point-source, diffractive properties of light to allow for detection of the perforate flaw 40.

Light 42, emanating from the virtual point source at defect 40, is communicated to the lens 34 as noted above. The lens means 34, in turn, provides a virtual image of light incident thereto to a video camera or means 46, suitably formed from a charged coupled device ("CCD"). Use of such a CCD array advantageously provides for acquisition of a digitized image which, in turn, is communicated to the computer 32. Such a digitized image is suitably compared against data representative of at least one of an acceptable container and a defective container to determine acceptability of the container associated therewith. Algorithms for such a comparison and determination are well within the understanding of ordinary skill in the art.

Many applications for container inspection require non-invasive, real-time inspection of containers which are in continuous motion relative to a stationary inspection station. However, a frozen or still image is advantageously obtained for completing defect analysis in such systems. The subject system provides alternative means to obtain such a frozen image. A first embodiment provides for strobing of the light source B under the control of the pulse control means 30. Such a strobe allows for exposure of the CCD array within camera means 460 After such a strobe, information is obtained from the CCD array which is related to the image as it existed during the brief illumination period. Alternatively, a high-speed electronic, mechanical or electro-mechanical shutter, disposed in conjunction with the lens means 34, may be utilized. Such a shutter allows for controlled exposure of the CCD array of camera 46, under the control of the computer 32 through control line 48. Alternative shuttering may be via a controllable CCD array or illumination control via a light valve on the illumination means B, such as in a liquid crystal light valve.

Figure 3:
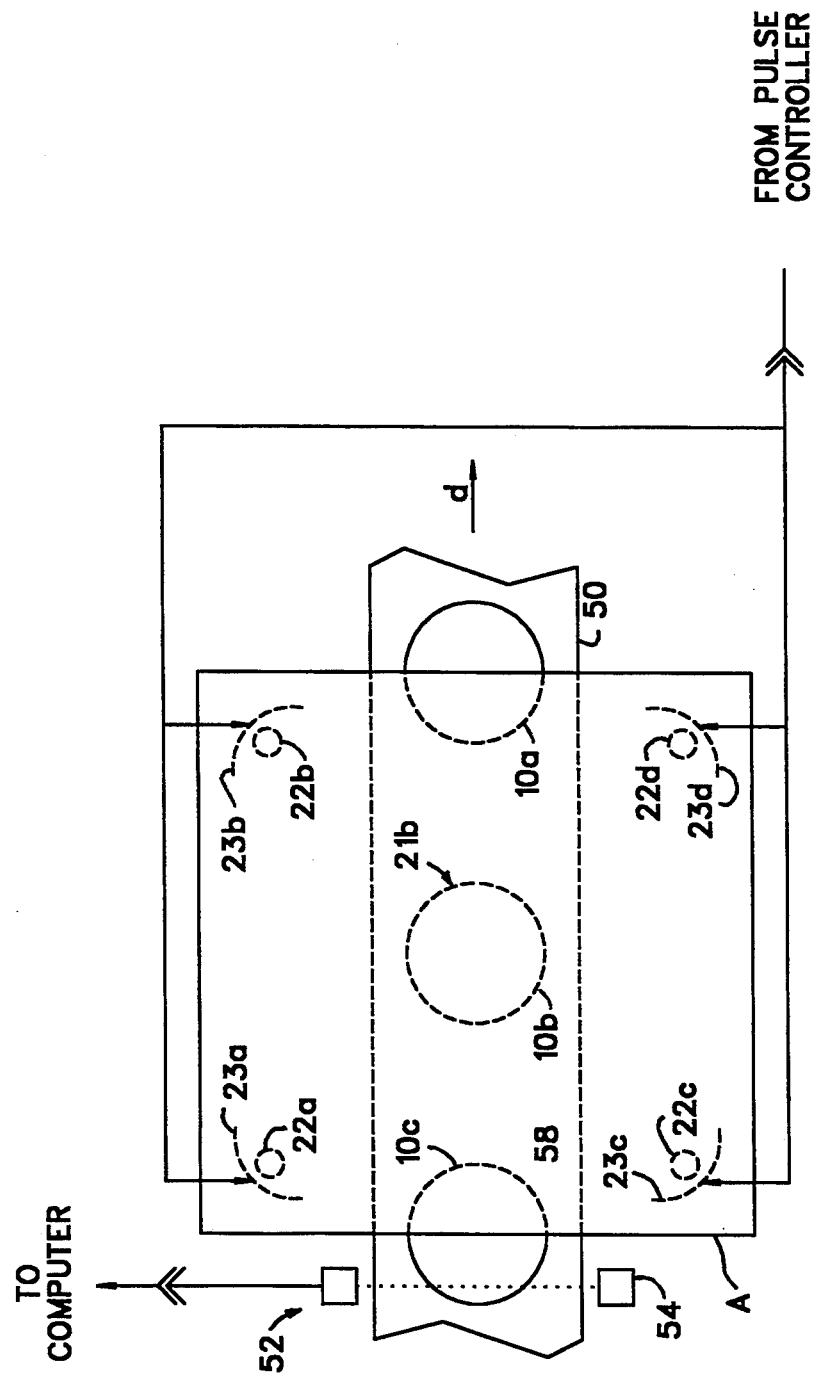
FIG. 3 illustrates a top view of an on-line inspection system in connection with the subject invention.

Turning now to FIG. 3, illustrated in a top view of an on-line inspection system as described above. A conveyor 50 communicates a series or sequence of specimens 10 along a direction d. In the illustration, the inspection system A defines therein inspection or lighting area indicated generally at 20. The light source B is defined as a circumspect light source inclusive of 4 strobe/reflectors 22a/23a–22d/23d. Each such pair is disposed relative to one another and to the lighting area 20 so as to substantially illuminate an entire exterior wall 21b of a specimen 10b illustrated as being disposed in the lighting area 20.

Progress of the specimens 10 on conveyor 50 relative to the inspection system A is tracked by a sensor 52 suitably formed as a photo-detection system comprised of a light source 54 and a photo detector 56.

As a specimen, such as that 10c illustrated, breaks beam 58, a signal is provided to the computer. The computer then calculates a rate of progress of the specimens along direction d to allow for timing of a flash of light source B (or alternatively enablement of a shuttering scheme associated with lens or image sensor 34) to allow capture of a still image. The light source B is enabled by the pulse control 30 (not shown). The camera 46 and lens 34 are removed from the illustration for purposes of clarity. However, it will be appreciated that the optical axis of the lens 34 is perpendicular to the illustration and progresses through the inspection or lighting area 20.

With the embodiment of FIG. 3, it will be seen that means for acquiring inspection for perforations throughout the side wall 21 of each specimen 10 is provided.

Figure 4:
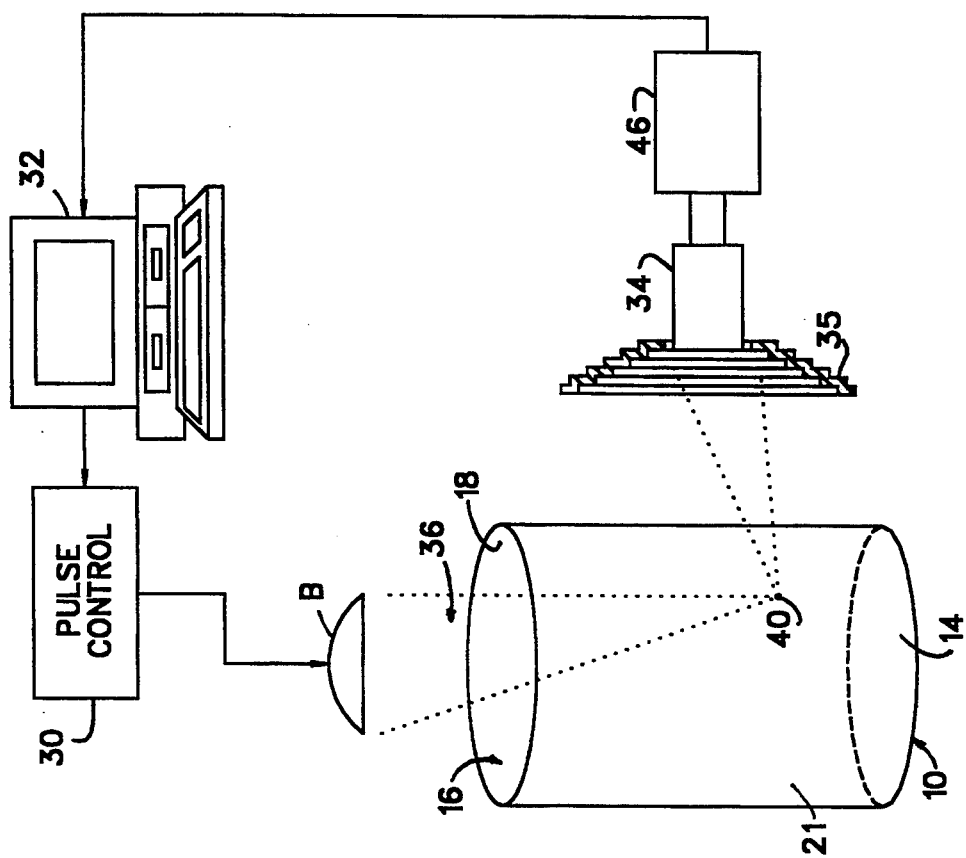
FIG. 4 illustrates a second embodiment of an inspection system in connection with the subject invention.

Turning now to FIG. 4, an alternative embodiment of a perforate defect inspection system as described above is provided. Therein, relative orientations of the camera 46 and its associated lens 34 and that of the light source B are interchanged. However, a direct radiation path between the light source B and the camera/lens is maintained. Discussion herein will be provided to illustrate the distinctions between this embodiment and that illustrated earlier. It will be appreciated that various components and subassemblies as illustrated above function identically and will not be described again.

The light source B is, again, suitably formed from an inert gas strobe or solid-snare illumination system. The light from the source B is directed to an interior of the specimen 10 through opening 16. Internal, reflective or scattering properties of the specimen 10 allow for illumination of an entire interior portion of the specimen by a single light source directed as shown. While a single light source is adequate in this embodiment, a plurality of cameras 46 may be required to allow for concurrent inspection of an entire side wall 21 of a specimen 10. While two such cameras may allow for acquisition of an image to an entire exterior surface, three or four cameras provide for a more direct capture of light emanating through a perforate defect.

Figure 5:
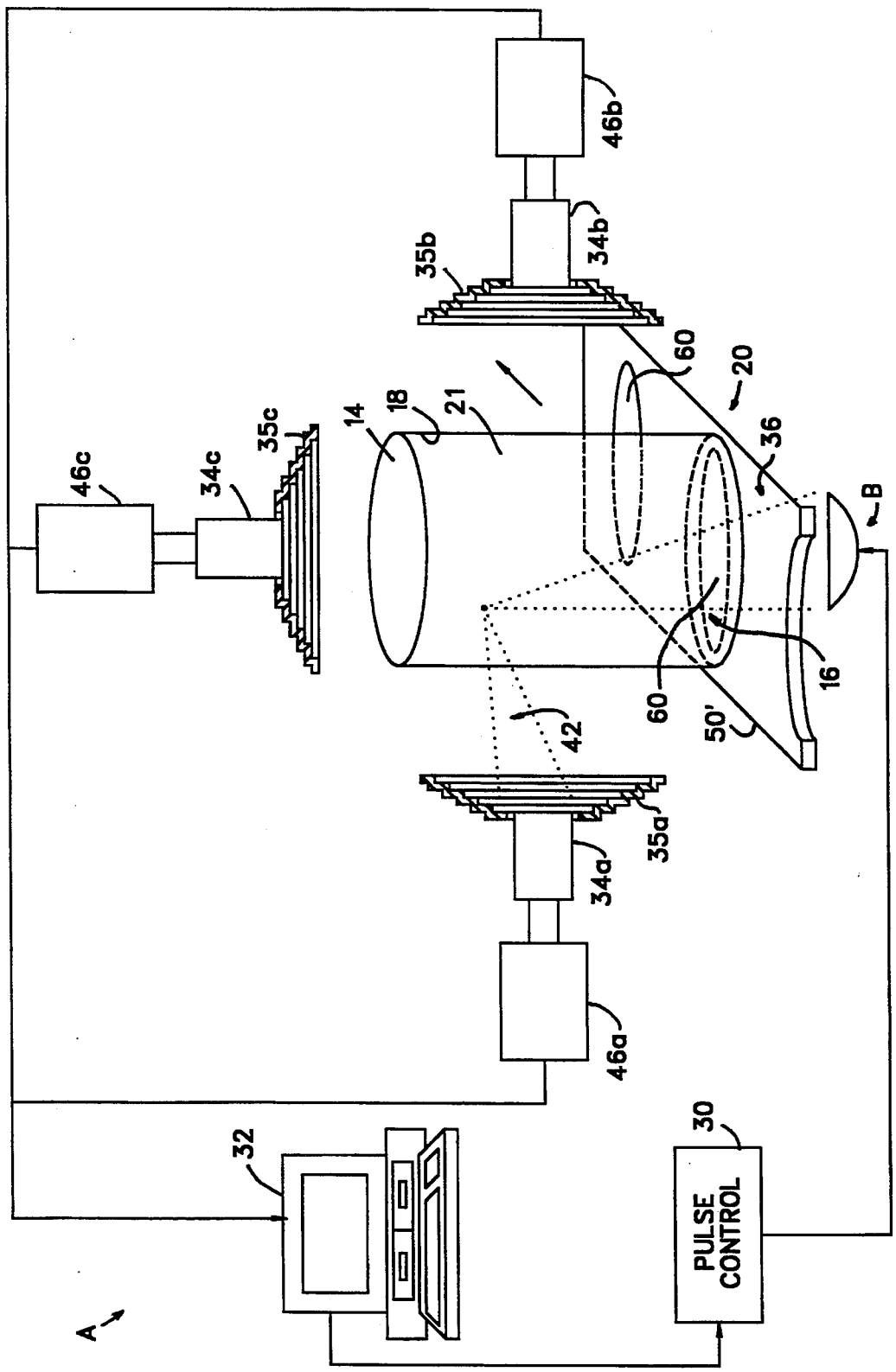
FIG. 5 illustrates an embodiment of the present invention employing illumination of an inverted container through a conveyor and employing bottom defect inspection.

Turning now to FIG. 5, disclosed is an embodiment employing illumination of an open container which is accomplished through the transporting conveyer 50'. In this invention, a series of associated apertures or translucent portions 60 provide illumination through opening 16 of each container 10 shown in an inverted position.

Also in the embodiment of FIG. 5, an additional camera 46c is mounted generally along an axis of the container 10, and in a direct path of illumination from light source B. In addition to the side-wall defect analysis, the addition of this camera facilitates analysis of perforate defects within the bottom wall 14 of the container. Although a direct illumination pass between the light source B and the camera/lens 46c/34c is provided, relatively small flaws will still result in the generation of a point source due to diffractive light properties.

This invention has been described with reference to preferred and alternate embodiments. Obviously, modifications and alterations will occur to others upon the reading and understanding of this specification. It is our intention to include all such modifications and alterations insofar as they come within the scope of the appended claims or the equivalents thereof.

Having thus described the invention, it is now claimed:

1. A perforate defect detection system comprising:
a light source;
securing means for securing the light source relative to an illumination area so as to illuminate at least a portion of an exterior surface of an opaque container disposed in the illumination area;
a conveyor communicating a generally continuous series of similar containers to the illumination area;
a detector detecting a presence of a container in the illumination area;
a camera for acquiring an image;
a lens means focusing light to the camera;
means for securing the lens such that the lens is directed to an interior of each container disposed in the illumination area and such that an optical axis of the lens is generally parallel to the exterior surface of a container disposed in the illumination area; and
shutter means for acquiring a still image of the interior of each container disposed in the illumination area such that a perforate defect in the exterior surface causes an artifact in the still image as a result of point source illumination from such perforate defect.

2. The perforate defect detection system of claim 1 wherein the shutter means is comprised of a strobe means for strobing the light source.

3. The perforate defect detection system of claim 1 wherein the shutter means is comprised of an electronic shutter in association with the lens.

4. The perforate defect detection system of claim 2 further comprising comparison means for comparing each acquired still image to data representative of at least one of an acceptable container and a defective container to determine container acceptability.

5. The perforate defect detection system of claim 4 further comprising means for isolating the interior surface of each container disposed in the illumination area from light other than light passing from the interior surface to the exterior surface through a perforate defect therebetween.

6. The perforate defect detection system of claim 5 wherein the light source circumscribes the container.

7. The perforate defect detection system of claim 6 wherein the plurality of individual lighting elements are disposed so as to concurrently illuminate substantially all of the exterior surface.

8. The perforate defect detection system of claim 7 wherein each of the individual lighting elements is formed from an inert gas strobe.

9. The perforate defect detection system of claim 7 wherein each of the individual lighting elements is formed from an array of solid state lighting elements.

10. The perforate defect detection system of claim 9 wherein each of the individual lighting elements are further formed from a laser source.

11. A perforate defect detection system comprising:
a light source for generating light along a general direction of propagation;
securing means for securing the light source relative to an illumination area so as to illuminate at least a portion of an interior surface of an opaque container disposed in the illumination area;
a conveyor communicating a generally continuous series of similar containers to the illumination area;
a detector detecting a presence of a container in the illumination area;
a camera for acquiring an image;
a lens focussing light to the camera;
means for securing the lens such that the lens is directed to at least a portion of an exterior surface, generally perpendicularly to the direction of propagation of light from the light source, of each container disposed in the illumination area; and
shutter means for acquiring a still image of the interior of each container disposed in the illumination area such that a perforate defect in the exterior surface causes an artifact in the still image as a result of point source illumination from such perforate defect.

12. The perforate defect detection system of claim 11 wherein the shutter means is comprised of a strobe means for strobing the light source.

13. The perforate defect detection system of claim 11 wherein the shutter means is comprised of an electronic shutter disposed within the lens.

14. The perforate defect detection system of claim 12 further comprising comparison means for comparing each acquired still image to data representative of at least one of an acceptable container and a defective container to determine container acceptability.

15. The perforate defect detection system of claim 14 further comprising means for isolating the exterior surface of each container disposed in the illumination area from light other than light passing from the interior surface to the exterior surface through a perforate defect therebetween.

16. The perforate defect detection system of claim 15 wherein the light source is formed from an inert gas strobe.

17. The perforate defect detection system of claim 15 wherein the light source is formed from an array of solid state lighting elements.

18. A method of detecting perforate defects in a wall of a container comprising the steps of:
communicating a generally continuous series of similar containers to an illumination area;
detecting a presence of an opaque container in the illumination area;
illuminating, via a light source, at least a portion of an exterior surface of each container disposed in the illumination area, which exterior surface is generally perpendicular to a direction of propagation of light from the light source;
isolating an interior portion of each container disposed in the illumination area from light of the light source;
acquiring an image, via a camera, of an interior portion of container having an exterior surface illuminated by the light source, an axis of the camera being generally perpendicular to the direction of propagation of light from the light source, such that a perforate defect in the exterior surface causes an artifact in the image as a result of point source illumination from such perforate defect.

19. The method of claim 18 wherein the step of acquiring an image includes the step of acquiring a still image of the interior portion of a container having an exterior surface illuminated by the light source.

20. The perforate defect detection system of claim 19 wherein the step of acquiring a still image includes at least one of enabling an electronic shutter associated with the camera and selectively strobing the light source.

21. The method of claim 20 further comprising the step of comparing each acquired still image to data representative of at least one of an acceptable container and a defective container to determine container acceptability.

22. The method of claim 21 wherein the step of illuminating includes the step of illuminating the at least a portion of an exterior surface of each container disposed in the illumination area via a plurality of individual lighting elements disposed so as to concurrently illuminate substantially all of the exterior surface.

23. The method of claim 22 wherein the step of illuminating further includes the step of illuminating the at least a portion of an exterior surface of each container disposed in the illumination area via a plurality of individual lighting elements, each of which includes an inert gas strobe.

24. The method of claim 22 wherein the step of illuminating further includes the step of illuminating the at least a portion of an exterior surface of each container disposed in the illumination area via a plurality of individual lighting elements, each of which includes an array of solid state lighting elements.

25. A method of detecting perforate defects in a wall of a container comprising the steps of:
communicating a generally continuous series of similar containers to an illumination area;
detecting a presence of a container in the illumination area;
illuminating, via a light source, an interior surface of each container disposed in the illumination area by providing light thereto generally along a preselected direction of propagation;
isolating an exterior portion of each container disposed in the illumination area from light of the light source;
acquiring an image, via a camera, of an exterior portion of container having an interior surface illuminated by the light source, an axis of the camera being disposed generally perpendicularly to the preselected direction of propagation such that a perforate defect in the exterior surface causes an artifact in the image as a result of point source illumination from such perforate defect.

26. The method of claim 25 wherein the step of acquiring an image includes the step of acquiring a still image of the exterior portion of a container having an interior surface illuminated by the light source.

27. The perforate defect detection system of claim 26 wherein the step of acquiring a still image includes at least one of enabling an electronic shutter associated with the camera and selectively strobing the light source.

28. The method of claim 27 further comprising the step of comparing each acquired still image to data representative of at least one of an acceptable container and a defective container to determine container acceptability.

29. The method of claim 28 wherein the step of illuminating includes the step of illuminating the at least a portion of an interior surface of each container disposed in the illumination area via a plurality of individual lighting elements disposed so as to concurrently illuminate substantially all of the interior surface.

30. The method of claim 29 wherein the step of illuminating further includes the step of illuminating the at least a portion of an interior surface of each container disposed in the illumination area via a plurality of individual lighting elements, each of which includes an inert gas strobe.

31. The method of claim 29 wherein the step of illuminating further includes the step of illuminating the at least a portion of an interior surface of each container disposed in the illumination area via a plurality of individual lighting elements, each of which includes an array of solid state lighting elements.

32. The method of claim 31 wherein the step of illuminating further includes the step of illuminating the at least a portion of an interior surface with light of a selected wavelength.

* * * * *